United States Patent [19]

Goldberg

[11] Patent Number: 4,990,596
[45] Date of Patent: Feb. 5, 1991

[54] SYNTHETIC PEPTIDE PRODUCING ANTIBODIES OF ENHANCED BINDING TO HUMAN LDH-C$_4$

[75] Inventor: Erwin Goldberg, Evanston, Ill.

[73] Assignee: Northwestern University, Evanston, Ill.

[21] Appl. No.: 311,477

[22] Filed: Feb. 16, 1989

[51] Int. Cl.$^5$ ................................................ C07K 7/08
[52] U.S. Cl. ........................................................ 530/327
[58] Field of Search ................ 530/327, 326, 328, 329

[56] References Cited

U.S. PATENT DOCUMENTS

| | | | |
|---|---|---|---|
| 4,290,944 | 9/1981 | Goldberg | 530/329 |
| 4,310,456 | 1/1982 | Goldberg | 530/328 |
| 4,353,822 | 10/1982 | Goldberg | 530/328 |
| 4,354,967 | 10/1982 | Goldberg | 530/328 |
| 4,377,516 | 3/1983 | Goldberg | 530/327 |
| 4,392,997 | 7/1983 | Goldberg | 530/327 |
| 4,782,136 | 11/1988 | Goldberg | 530/326 |

*Primary Examiner*—Lester L. Lee
*Assistant Examiner*—Sandra G. Marshall
*Attorney, Agent, or Firm*—Tilton, Fallon, Lungmus & Chestnut

[57] ABSTRACT

A synthetic peptide producing antibodies of enhanced binding to the human C$_4$ isozyme of lactate dehydrogenase (LDH-C$_4$) is composed of amino acids corresponding to the 9 to 20 sequence of the human enzyme. The peptide can be used as the active component of an antifertility vaccine for women.

1 Claim, No Drawings

SYNTHETIC PEPTIDE PRODUCING ANTIBODIES OF ENHANCED BINDING TO HUMAN LDH-C$_4$

FIELD OF INVENTION

The field of this invention is synthetic peptide compounds capable of producing antibodies to the lactate dehydrogenase enzyme of mammalian semen (LDH-C$_4$). Such peptides can be used to prepare vaccines for reducing fertility of women.

BACKGROUND OF INVENTION

Mammalian spermatozoa have been known to be antigenic for many years. More recently, it has been demonstrated that mammalian sperm contain an antigenic enzyme, which is known as the C$_4$ isozyme of lactate dehydrogenase (LDH-C$_4$). LDH-C$_4$ has been isolated in pure crystalline form from mouse testes. Goldberg (1972), *J. Biol. Chem.*, 2247:2044–2048. The enzyme has a molecular weight of about 140,000 and is composed of four identical C subunits. The amino acid sequence and three-dimensional structure of mouse LDH-C$_4$ have been studied and described by a number of investigators: Musick, et al., (1976), *J. Mol. Biol.*, 104:659–668; Wheat, et al. (1977), *Biochem. & Biophys. Res. Comm.* 74, No. 3:1066–1077; Li, et al. (1983), *J. Biol. Chem.* 258:7017–7028; and Pan, et al. (1983), *J. Biol. Chem.* 258:7005–7016.

In 1974, Dr. Erwin Goldberg reviewed the effects of immunization with LDH-X (LDH-C$_4$) on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties makes the immunological approach to fertility control feasible". *Karolinska Symposia on Research Methods in Reproductive Endocrinology* 7th Symposium: Immunological Approaches to Fertility Control, Geneva, 1974, 202–222.

Subsequent investigations by Dr. Goldberg and his research associates identified several amino acid sequences of mouse LDH-C$_4$ which in synthetic form (e.g., as short chain polypeptides) bind to LDH-C$_4$ antiserum. See Wheat, et al. (1981), in Rich, et al., *Peptides: Synthesis-Structure-Function, Proc. 7th Amer. Peptide Symp.*, pp. 557–560; and Gonzales-Prevatt, et al. (1982), *Mol. Immunol.* 19:1579–1585. Several antigenic peptide compounds based on these sequences have been patented. See U.S. Pat. Nos. 4,290,944; 4,310,456; 4,353,822; 4,377,516; 4,392,997; 4,278,519; and 4,585,587.

The antigenic peptides based on sequences of mouse LDH-C$_4$ are potentially useful in preparing vaccines to reduce female fertility. Immunization of female mammals results in the development of circulating antibodies specific to LDH-C$_4$. These immunoglobulins reach the female reproductive tract as a transudate of serum: Kille, et al. (1977), *Biol. Reprod.* 20:863–871. Antibody in cervical mucus, uterine fluids, and oviducal fluids combine with LDH-C$_4$ on the sperm surface and impede the progress of the male gamete, presumably by agglutination. Systemic immunization with LDH-C$_4$ markedly interferes with sperm transport in the female reproductive tract: Kille et al. (1980), *J. Reprod. Immunol.*, 2:15–21.

The 1983 status of research on LDH-C$_4$ and antigenic peptides for use in female contraceptive vaccines was summarized in two publications by the Goldberg group: Goldberg, et al. (1983), In *Immunology of Reproduction*, Chapt. 22, pp. 493–504; and Wheat, et al. (1983), in *Isozymes: Current Topics in Biological and Medical Research*, Vol. 7, pp. 113–140. The synthetic peptide corresponding to the mouse LDH-C$_4$ sequence 5 to 15 (which included 16 amino acids because of Glu-14a and Asp-14b) was selected as a promising peptide for immunization studies. Wheat, et al. (1985), *Molec. Immun.* 22:1195–1199; and Goldberg and Shelton, in "Immunological Approaches to Contraception and Promotion of Fertility", pages 219–230 (ed. G. P. Talwar, Plenum Publishing Corp., 1986) and U.S. Pat. No. 4,392,997. With the peptide identified as mouse (MC) 5-15 immunization studies were conducted with female baboons. The results obtained indicated a 71% reduction in fertility, but in commenting thereon, Goldberg and Shelton stated (at page 225):

"While these results demonstrate the promise that this approach holds, the percentage of fertility reduction must be increased to a level acceptable for human contraceptive practice. Certainly, one possibility is that, while MC5-15 immunization is effective in reducing fertility, another peptide or combination of peptides might be more immunogenic."

One approach pursued by Dr. Goldberg and his colleagues to improve antifertility immunogenicity of the proposed vaccines was to determine the sequences of human LDH-C$_4$. The human gene for Ldh-c was isolated, cloned, and sequenced: Millan, et al. (1987), *Proc. Natl. Acad. Sci. USA*, 84: 5311–5319. This led to the discovery that the human sequences of the LDH-C$_4$ enzyme corresponding to the previously-identified antigenic sequences of mouse LDH-C$_4$ differed markedly with respect to amino acid content. The comparative sequences are illustrated in Millan, et al., cited above, at page 5314, and in Goldberg and Millan U.S. Pat. No. 4,782,136. The 16 number sequence of the human enzyme corresponding to the mouse sequence 5-15 differed by six amino acids, as illustrated in column 3 of the cited Goldberg and Millan patent.

SUMMARY OF INVENTION

Based on the extensive research with the mouse LDH-C$_4$ sequence 5 to 15, it was expected that the corresponding human sequence (numbered 5 to 16) defined a highly antigenic region. Further, since the human 5 to 16 sequence contained six different amino acids from the mouse 5 to 15 sequence, it was expected that the synthetic peptide for human 5 to 16 would produce antisera containing antibodies which bind more effectively to human LDH-C$_4$. This prediction was confirmed by data showing that the immune response was increased by several fold over the mouse-based peptide.

The present invention is based on a further discovery, namely, that a synthetic peptide corresponding to the human 9 to 20 sequence unexpectedly provides greatly enhanced antibody binding response to human LDH-C$_4$ as compared with the synthetic peptide corresponding to the human 5 to 16 sequence. The antibodies produced by the human 9–20 synthetic peptide bind more effectively to the human enzyme by two to three orders of magnitude. These dramatic results also indicate that the human 9 to 20 sequence when used as an antifertility vaccine will provide enhanced immunogenicity. Further, the data strongly suggests that the antibodies will have improved specificity, that is, cross-reactions with somatic LDH-A or LDH-B will be avoided.

DETAILED DESCRIPTION

The relevant amino acid sequences of human and mouse LDH-C$_4$ are compared in Diagram A.

DIAGRAM A
Comparison of a Homologous Segment of Human LDH-C with Mouse LDH-C Human[a][c]

| 5 | | 9[d] | 10 | 11 | 12 | 14 | 15 | 16 | 17 | | 19 | 20 |
|---|---|---|---|---|---|---|---|---|---|---|---|---|
| Glu—Gln—Leu—Ile—Glu—Lys—Leu—Ile—Glu—Asp—Asp—Glu—Asn—Ser—Gln—Cys |

| Glu—Gln—Leu—Ile—Gln—Asn—Leu—Val—Pro—Glu—Asp—Lys—Leu—Ser—Arg—Cys |
| 5 | | 9 | 10 | 11 | | 14a | 14b | 15 | 16 | | 18 | 19 |

Mouse[b][c]

[a]Human sequence numbering follows Millan, et al. (1988) Proc. Natl. Acad. Sci. U.S.A., 84:5311-5315.
[b]Mouse sequence numbering follows Wheat and Goldberg (1985), Annals N.Y. Acad. Sci., 438:156-169, which used Pro-13, Glu-14a, Asp-14b, Lys-15. Human Asp-14 and Asp-15 respectively correspond with mouse Glu-14a and Asp-14b.
[c]Standard three letter abbreviations are used for the amino acids as follows: Arg—arginine, Asn—asparagine, Asp—aspartic acid, Cys—cysteine, Gln—glutamine, Glu—glutamic acid, Ile—isoleucine, Leu—leucine, Lys—lysine, Pro—proline, Ser—serine, and Val—valine.
[d]The human amino acids which differ from the corresponding mouse amino acids are underscored.

As can be seen in Diagram A, the human sequence from 5 to 16 contains six different amino acids from the corresponding mouse sequence 5 to 15. Also, in the human sequence from 17 to 20, Asn-17 differs from Leu-16 and Gln-19 from Arg-18, which differences are especially significant. Glutamine-18 is a neutral or uncharged amino acid while arginine-18 is positively charged. Asparagine-17 is of considerably larger molecular size than leucine-16.

The synthetic peptide of this invention is illustrated in Diagram B.

DIAGRAM B

Amino Acid Sequence[a] for Antigenic Peptide[b]

Glu-Lys-Leu-Ile-Glu-Asp-Asp-Glu-Asn-Ser-Gln-Cys (a) Standard three letter abbreviations are used, as in Diagram A. (See footnote b of Diagram A.)
(b) Sequence represents linear peptide from N-terminal Glu to C-terminal Cys.

The peptide of Diagram B contains 12 amino acids arranged in linear sequence from N-terminal to C-terminal. This peptide is therefore composed in sequence of the following amino acids glutamic acid-lysine-leucine-isoleucine-glutamic acid-aspartic acid-aspartic acid-glutamic acid-asparagine-serine-glutamine-cysteine. This peptide can be synthesized by known procedures and with known apparatus. For example, the synthesis can be carried out by the Merrifield Solid Phase Method as described in J.A.C.S. (1963), 85:2149–2154, or Stewart and Young, "Solid Phase Peptide Synthesis" (W. H. Freeman & Co., San Francisco, 1969, pp. 1–4). Commercially available synthesizers which can be used for preparing the peptide of this invention include the Peptide Synthesizer, Model 430A, of Applied Biosystems, Inc., Foster City, Calif.

To utilize the antigenic peptide of this invention in the form of a fertility reducing vaccine, the peptide is conjugated to a carrier molecule, which is preferably a protein which itself elicits an antigenic response and which can be safely administered. A suitable procedure for preparing the peptide in conjugated form for vaccine use is described in Wheat, et al. (1985), cited above.

EXPERIMENTAL BASIS OF INVENTION

Following the synthesis of the peptide of this invention, designated HC 9-20, it was tested in a comparative experiment against the synthetic peptides, respectively, corresponding to mouse 5-15 (MC 5-15), human 1-16 (HC 1-16), and human 5-16 (HC 5-16). Each peptide was conjugated to a carrier as described in Wheat et al. (1985), cited above. Diphtheria toxoid was used as the carrier.

The conjugated peptides were administered to rabbits as follows: 0.1 ml of antigen at 2 mg/ml emulsified 1:1 with Freund's Complete Adjuvant (CFA) wa injected at multiple sites subcutaneously. Four weeks later a booster injection consisting of 0.1 ml antigen at 2 mg/ml in an equal volume of Incomplete Freund's Adjuvant (ICFA) was similarly injected. CFA and ICFA were obtained commercially (Calbiochem Inc.) and sterile techniques were used. Blood was collected at two week intervals from the median artery of the ear, allowed to clot, and the serum removed with a dispo pipette. Sera were aliquotted and stored frozen at −20° C. Antigens injected were MC5-15, HC1-16, HC5-16, and HC9-20, each conjugated to diphtheria toxoid by the procedure previously described (Wheat, Shelton and Goldberg, 1985).

Antisera from at least two rabbits for each peptide were pooled and titered against recombinant human LDH-C$_4$.

Antibody titers were determined by ELISA. Flexible polyvinyl chloride microtiter plates (Dynatech) were incubated with $10^7$M solutions of mouse or human LDH-C$_4$ in 0.1M carbonate buffer pH 9.6 at 4° C. overnight. After blocking for 2 hours in 1% bovine serum albumin (BSA) in 0.05M Tris 0.15M sodium chloride, pH 8.0 (TBS), 3-fold serial dilutions of the antibody samples in 1% BSA in 0.01M sodium phosphate, 0.15M sodium chloride (PBS) were added to the wells and incubated at room temperature for 1 hour. The plates were washed three times in TBS. Peroxidase-conjugated goal anti-mouse IgG (Miles Laboratories) was incubated for an additional hour at room temperature, and visualized with 1 mM 2,2' a zino-d-(3-ethyl-benzothiasolin sulfonate (ABTS)/0.003% hydrogen peroxide as substrate in 0.05M citrate/sodium phosphate buffer pH 4.0. The reaction was stopped after 10 minutes by the addition of 1% SDS and absorbance (410 nm) recorded on a Dynatech ELISA reader. Titer is defined as the reciprocal of the serum dilution which gives 0.5 absorbance units over normal serum background. Using a similar procedure, the antisera was tested against mouse LDH-$C_4$. The results obtained are summarized below in Table A.

TABLE A

| Immunogen | Antibody Titers | |
| --- | --- | --- |
|  | $MC_4$ | $HC_4$ |
| None | 10 | 30 |
| MC 5-15 | >30,000 | 600 |
| HC 1-16 | 200 | 1,500 |
| HC 5-16 | 250 | 7,000 |
| HC 9-20 | n.d. | 280,000 |

The foregoing results demonstrate the greatly enhanced binding of antibodies generated by the synthetic peptide of this invention (HC 9-20) as compared with the other synthetic peptides tested. When tested against the human enzyme ($HC_4$), the antibody titer determined was 280,000 as compared with the antibody titer of 7,000 for HC 5-16, showing two to three orders of magnitude greater binding effectiveness for the antibodies provoked by HC 5-16. The magnitude of this response to the HC 9-20 antibodies resulting from higher avidity of the antibodies for the LCH-$C_4$ antigen, also indicates that the HC 9-20 should be highly specific for LDH-$C_4$, and that cross-reactions with LDH-A or LDH-B will not occur.

I claim:

1. A synthetic peptide compound capable of producing antibodies of enhanced binding to the lactate dehydrogenase enzyme of human semen, which consists essentially of the N-terminal to C-terminal sequence represented by:

Glu-Lys-Leu-Ile-Glu-Asp-Asp-Glu-Asn-Ser-Gln-Cys wherein Asn, Asp, Cys, Gln, Glu, Ile, Leu, Lys, and Ser respectively are asparagine, aspartic acid, cysteine, glutamine, glutamic acid, isoleucine, leucine, lysine, and serine.

* * * * *